(12) United States Patent
Fogwill et al.

(10) Patent No.: US 10,274,463 B2
(45) Date of Patent: Apr. 30, 2019

(54) STATIC SPATIAL THERMAL GRADIENTS FOR CHROMATOGRAPHY AT THE ANALYTICAL SCALE

(71) Applicant: Waters Technologies Corporation, Milford, MA (US)

(72) Inventors: Michael O. Fogwill, South Grafton, MA (US); Abhijit Tarafder, Franklin, MA (US); Joseph D. Michienzi, Plainville, MA (US); Joshua A. Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 225 days.

(21) Appl. No.: 15/062,430

(22) Filed: Mar. 7, 2016

(65) Prior Publication Data

US 2016/0266077 A1 Sep. 15, 2016

Related U.S. Application Data

(60) Provisional application No. 62/131,317, filed on Mar. 11, 2015.

(51) Int. Cl.
*G01N 30/30* (2006.01)

(52) U.S. Cl.
CPC ....... *G01N 30/30* (2013.01); *G01N 2030/303* (2013.01); *G01N 2030/3015* (2013.01); *G01N 2030/3053* (2013.01)

(58) Field of Classification Search
CPC . G01N 30/30; G01N 30/54; G01N 2030/3015
(Continued)

(56) References Cited

U.S. PATENT DOCUMENTS 4,484,061 A * 11/1984 Zelinka ................. G01N 30/30
137/341
5,005,399 A * 4/1991 Holtzclaw .............. G01N 30/30
73/23.39
(Continued)

OTHER PUBLICATIONS

Contreras, Jesse Alberto, Axial Temperature Gradients in Gas Chromatography, Sep. 2, 2010, Thesis, Brigham Young University.*
(Continued)

*Primary Examiner* — Lisa M Caputo
*Assistant Examiner* — Irving A Campbell
(74) *Attorney, Agent, or Firm* — Schmeiser, Olsen & Watts LLP

(57) ABSTRACT

Analytical-scale separation column assemblies include a tube with a bore packed with a stationary phase through which a mobile phase flows. In one embodiment, thermal elements are disposed remotely from and unattached to the tube. The thermal elements are in thermal communication with an external surface of the tube for producing a spatial thermal gradient outside of and along a length of the tube. In another embodiment, discrete, spatially separated strips of thermally conductive material are disposed on and wrapped around an external surface of the tube. Thermal elements are disposed remotely from the tube. Each thermal element is in thermal communication with one strip of thermally conductive material by a heat-transfer device. The thermal elements produce a spatial thermal gradient outside of and along a tube length by controlling temperature of each strip of thermally conductive material disposed on and wrapped around the external surface of the tube.

18 Claims, 11 Drawing Sheets

(58) Field of Classification Search
USPC .......... 73/23.26, 23.35, 61.52, 61.53, 61.57, 73/51.53; 95/87
See application file for complete search history.

(56) References Cited

U.S. PATENT DOCUMENTS

| | | | | |
|---|---|---|---|---|
| 5,135,549 | A * | 8/1992 | Phillips | G01N 30/30 210/198.2 |
| 5,215,556 | A * | 6/1993 | Hiller | G01N 30/30 95/87 |
| 5,808,178 | A * | 9/1998 | Rounbehler | G01N 30/30 73/23.35 |
| 7,530,259 | B2 * | 5/2009 | Tai | G01N 30/30 73/61.52 |
| 9,678,046 | B2 * | 6/2017 | Tolley | G01N 30/30 |
| 2003/0145725 | A1 * | 8/2003 | Hastings | G01N 30/30 95/87 |
| 2010/0005867 | A1 * | 1/2010 | Doerr | B01L 3/5027 73/61.53 |
| 2012/0318782 | A1 | 12/2012 | Collins et al. | |

OTHER PUBLICATIONS

Tarafder, Abhijit and Georges Guiochon, "Use of isopycnic plots in designing operations of a supercritical fluid chromatography: II. The isopycnic plots and the selection of the operating pressure-temperature zone in supercritical fluid chromatography", Journal of Chromatography A, 2011, pp. 4576-4585, vol. 1218, Elsevier B.V.

* cited by examiner

STATIC SPATIAL THERMAL GRADIENTS FOR CHROMATOGRAPHY AT THE ANALYTICAL SCALE

RELATED APPLICATION

This application claims priority to U.S. Provisional Application Ser. No. 62/131,317, filed on Mar. 11, 2015 entitled "STATIC SPATIAL THERMAL GRADIENTS FOR CHROMATOGRAPHY AT THE ANALYTICAL SCALE", the entirety of which is incorporated by reference herein.

FIELD OF THE INVENTION

The invention relates generally to chromatography systems. More specifically, the invention relates to apparatuses and methods for establishing spatial thermal gradients around a separation column to counter the formation of radial temperature gradients within the column and, thus, mitigate or eliminate a cause of chromatographic band broadening.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. The mobile phase comprised of a sample dissolved in a mixture of solvents (and/or other fluids), moves to a point of use, such as a separation column, referred to as the stationary phase. By passing the mobile phase through the column, the various components in the sample separate from each other at different rates and thus elute from the column at different times. A detector receives the separated components from the column and produces an output from which the identity and quantity of the analytes may be determined.

Temperature can influence the results of the analysis, affecting such properties as the separation performance of the column and the viscosity of a mobile phase. Forcing a liquid phase (i.e., relatively non-compressible) through a packed bed column causes an increase in mobile phase temperature because of frictional (i.e., viscous) heating. Because thermal energy can be dissipated only through the outer surface of the column, a radial temperature gradient is formed within the column, with a warmer region being near the center of the column.

When employing compressible mobile phases a similar phenomenon occurs. In this instance, at certain regions of the phase diagram, an inverse radial temperature gradient (cooler near the center of the column) forms, caused by Joule-Thompson cooling of the mobile phase as it decompresses along the length of the column. Accordingly, the mobile phase cools as it travels along the length of the column. Because a column oven holds the outside of the column at a consistent temperature, radial temperature gradients are most severe near the outlet of the column, (i.e., where the mobile phase is coldest relative to the column exterior temperature). In both instances of heating and cooling, the magnitude of the radial temperature gradient increases as the diameter of the stationary phase particles decreases.

The formation of on-column radial temperature gradients causes a decrease in chromatographic performance. Because density, solvating power, viscosity, and analyte diffusivity, to name just a few properties, all depend on mobile phase temperature, a radial temperature gradient results in changes in analyte mobility across the cross-section of the column. Changes in analyte mobility result in regions of the analyte (i.e., chromatographic) band travelling faster or slower through the column than the bulk of the analyte band. This heterogeneity in analyte velocity results in broadening of the analyte band and, therefore, in a reduction of chromatographic efficiency. Therefore, minimizing the effects of radial thermal gradients in a column can be important to the accuracy and reproducibility of the results.

In addition to the formation of radial thermal gradients in SFC, linear velocity of the mobile phase can increase along the length of the column, which can have a negative effect on peak width. The pressure drop along the column results in a reduction in the $CO_2$ density. Because the mass flow rate is conserved, a drop in density results in an increase in mobile phase linear velocity. The increase in the linear velocity will result in moving toward less efficient regions of a van Deemter curve. This change in linear velocity, although not observed with relatively incompressible mobile phases, such as is used in liquid chromatography (LC), has been a reason suggested for not using sub-2 μm particles with compressible mobile phases, such as is used in SFC.

SUMMARY

All examples and features mentioned below can be combined in any technically possible way.

In one aspect, a separation column assembly is featured comprising a tube with a bore packed with a stationary phase through which a mobile phase flows, and one or more thermal elements disposed remotely from and unattached to the tube. The one or more thermal elements are in thermal communication with an external surface of the tube for producing a spatial thermal gradient outside of and along a length of the tube.

Embodiments of the separation column assembly may include one of the following features, or any combination thereof.

The separation column assembly may further comprise a sleeve disposed around the tube. The sleeve is open at both ends and separated from the tube by an air gap through which a gas flows. The one or more thermal elements are in thermally conductive communication with an outside surface of the sleeve. The one or more thermal elements may comprise heating elements that heat the sleeve, wherein the gas flowing through the air gap is a cooling gas. The one or more thermal elements may comprise cooling elements that cool the sleeve, wherein the gas flowing through the air gap is at least as high as ambient temperature. The separation column assembly may further comprise a plurality of discrete, spatially separated strips of thermally conductive material disposed on and wrapped around the outside surface of the sleeve, wherein the one or more thermal elements comprise a plurality of thermoelectric devices. Each thermoelectric device is in thermal communication with one of the thermally conductive elements disposed on the sleeve by a heat-transfer device.

The bore of the tube of the separation column assembly may have an inner diameter ranging between 1.0 and 5.0 mm, inclusively. One or more of the thermal elements may be configured to operate as a cooling device or as a heating element.

The separation assembly may further comprise a thermal controller in communication with the one or more thermal elements. The thermal controller may be configured to dynamically control the spatial thermal gradient. The separation column assembly may further comprise a database in communication with the thermal controller, the database containing thermodynamic properties of the separation column assembly.

In another aspect, a separation column assembly is featured comprising a tube with a bore packed with a stationary phase through which a mobile phase flows, a plurality of discrete, spatially separated strips of thermally conductive material disposed on and wrapped around an external surface of the tube, and a plurality of thermal elements disposed remotely from the tube. Each of the one or more thermal elements is in thermal communication with one of the strips of thermally conductive material by a heat-transfer device. The thermal elements produce a spatial thermal gradient outside of and along a length of the tube by controlling temperature of each strip of thermally conductive material disposed on and wrapped around the external surface of the tube.

Embodiments of the separation column assembly may include one of the following features, or any combination thereof.

The separation column assembly may further comprise a sleeve disposed around the tube. The sleeve is open at both ends and separated from the tube by an air gap through which a gas flows, wherein the one or more thermal elements are in thermally conductive communication with an outside surface of the sleeve. The one or more thermal elements may comprise heating elements that heat one or more of the strips of thermally conductive material, or cooling elements that cool one or more of the strips of thermally conductive material. The plurality of thermal elements may comprise a plurality of thermoelectric devices.

In still another aspect, a separation column assembly is featured comprising a tube with a bore packed with a stationary phase through which a mobile phase flows. The tube has an external surface with a plurality of spatially separated heating elements formed thereon. The separation column assembly further comprises a pair of electrical contacts coupled to each heating element for independently operating that heating element.

Embodiments of the separation column assembly may include one of the following features, or any combination thereof.

Each heating element may wraps circumferentially around the tube. The one or more heater elements may include a substantially triangular-shaped heater having a narrow end and a wide end. The triangular-shaped heater produces a spatial thermal gradient that is warmer at the narrow end than at the wide end, and is disposed on one side of the external surface of the tube. The one or more heater elements may further include a substantially rectangular-shaped heater that produces a substantially uniform spatial thermal gradient. The rectangular-shaped heater is disposed on the external surface of the tube on a side opposite the triangular-shaped heater.

In yet another aspect, a multi-zone heater assembly is featured comprising a thermally conductive column block, a separation column extending through and in thermal communication with the thermally conductive column block, a thermally conductive thermal block in thermal communication with the thermally conductive column block, and a plurality of independently operable heaters embedded in the thermal block. Each heater produces a temperature for a different zone of the multi-zone heater assembly. The independently operable heaters together produce a spatial thermal gradient in the thermally conductive column block that surrounds a length of the separation column.

Embodiments of the multi-zone heater assembly may include one of the following features, or any combination thereof.

The multi-zone heater assembly may further comprise an insulator embedded in the thermally conductive thermal block thermally isolating each neighboring pair of thermal zones from each other within the thermally conductive thermal block.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
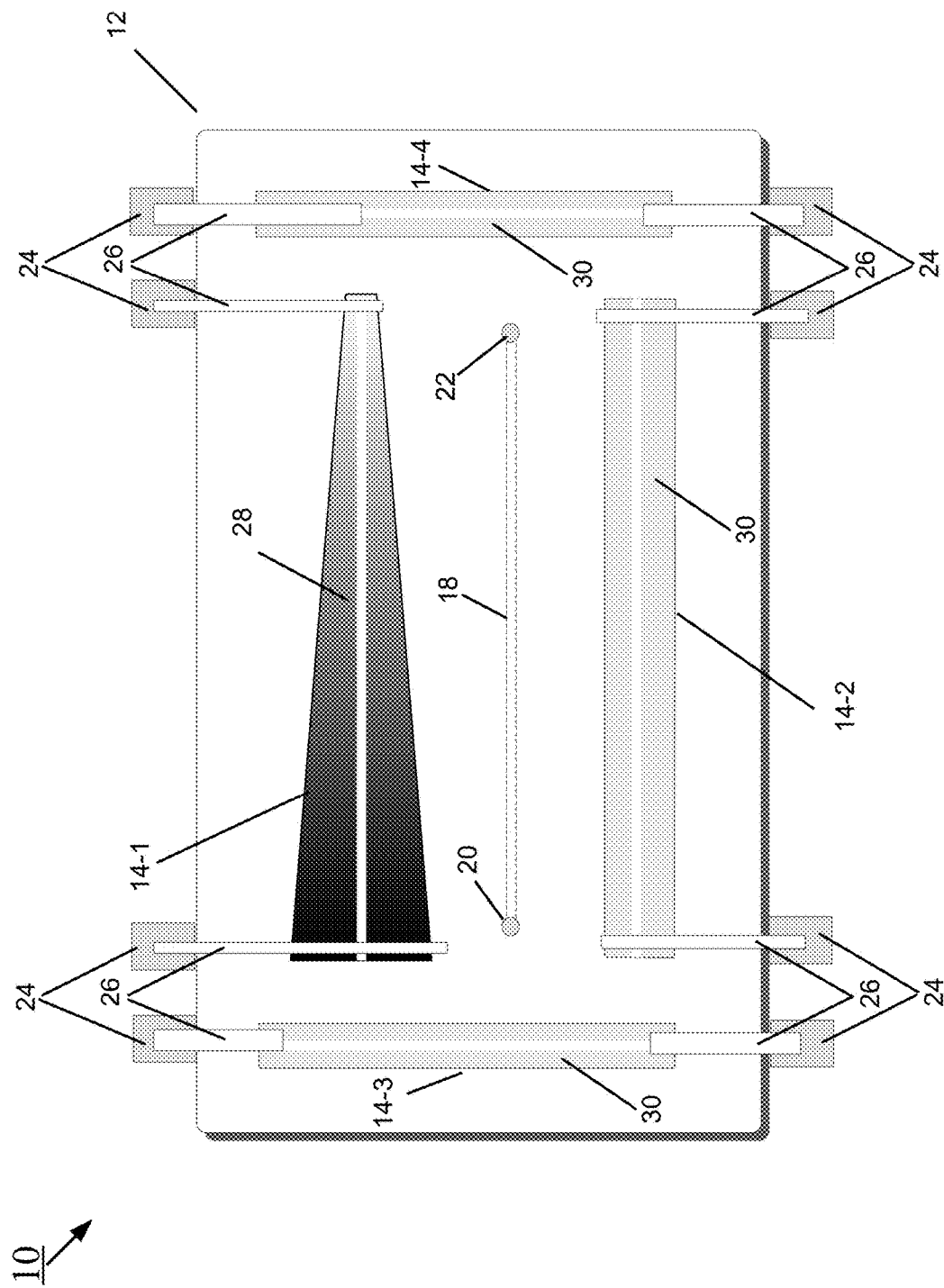
FIG. 1 is a diagram of an embodiment of a thermal system for producing a spatial thermal gradient near a fluidic channel (e.g., a separation column) in a microfluidic device using two thick-film heaters, specifically, a trapezoidal heater and a rectangular heater, in conjunction.

The ability to form static spatial thermal gradients has shown promise for improved gas chromatography separations. Such gradients are relatively easy to establish in gas chromatography because of the ability to integrate heating elements directly onto the surface of the separation column. Similarly, these gradients can be established in microfluidic chromatography with relative ease. Complications arise, however, when spatial thermal gradients are to be implemented at the analytical scale. For example, the comparatively large thermal mass of an analytical scale liquid chromatography or supercritical fluid chromatography column requires specialized heating. Further, to keep the consumable costs down and enable the ability to frequently replace columns suggests that the heating elements not be integrated with the column itself, but instead be a component of the column heater component of the separation system. In addition, separating the column from the column heater helps to reduce the cost of the consumable separation column.

Analytical-scale separation column assemblies described herein produce a spatial thermal gradient to address two sources of band broadening: radial thermal gradients in liquid chromatography (LC) columns and compressible fluid chromatography (CFC) columns; and linear velocity increases across a CFC column. The types of separation columns subject to the formation of radial thermal gradients include, but are not limited to, analytical scale chromatography columns (e.g., 2.1-4.6 mm i.d.); preparative scale chromatography columns (e.g., approximately 7 to 100 mm i.d.); those subject to increasing linear velocity include analytical scale columns and fluidic channels formed in the layers of a microfluidic device. A varying temperature produced externally and longitudinally along the column forms such spatial thermal gradients. To produce a spatial thermal gradient along a column, a variety of techniques may be employed, including, for example, heating near and around the separation column with one or more resistive heaters, passing a cooling gas over the separation column, and extending the separation column through a multi-zone heater assembly.

For example, if, as the mobile phase travels the length of the separation column it is expected to cool, as in the instance of a compressible mobile phase, a spatial thermal gradient is formed on the exterior of the column to be warmer at the head entry of the column and cooler at the exit end of the column. This "cooling" spatial thermal gradient formed on the immediate exterior of the column is designed to substantially match an expected (or estimated) cooling thermal gradient formed by the mobile phase within the column. Accordingly, the temperature in the column interior substantially matches the temperature on the immediate exterior of the column, thereby minimizing the magnitude of any radial thermal gradient that may form within the column and improving the chromatographic efficiency.

A cooling spatial thermal gradient can also be used to control the linear velocity of the mobile phase as it passes through the column. For example, CFC systems use a highly compressible mobile phase, which increases in linear velocity as it passes through the column, when the column is maintained within a constant thermal environment (i.e., column oven). A spatial thermal gradient formed exterior of the column to be warmer at the head entry of the column and cooler at the exit end of the column can operate to make the linear velocity of the mobile phase substantially constant along the length of the column.

Alternatively, if, as the mobile phase travels the length of the column it is expected to warm, as in the instance of an incompressible mobile phase and in some instances of SFC where the mobile phase is relatively incompressible (i.e., at high pressure and/or low temperature), a spatial thermal gradient is formed on the exterior of the column to be cooler at the head entry of the column and warmer at the exit end of the column. This increasingly warm spatial thermal gradient formed on the immediate exterior of the column is designed to substantially match an expected increasingly warmer thermal gradient within the column. Again, as a result, the temperature in the column interior substantially matches the temperature on the immediate exterior of the column, thereby minimizing the magnitude of any radial thermal gradient that may form within the column and improving the chromatographic efficiency.

Thermodynamic modeling may be used to estimate or predict the degree of a thermal gradient that forms within a column in response to the passing of a mobile phase, and to estimate the magnitude of any consequent radial thermal gradient if the column (such as an analytical scale column) were to be maintained in a constant thermal environment. Thermodynamic modeling may also be used to estimate the change in temperature needed to maintain the mobile phase at a constant density along the length of the column, to thereby keep the mobile phase at a constant linear velocity.

Control of the formation of the spatial thermal gradient can occur in open loop or closed loop fashion. A closed-loop system for temperature control of the spatial gradient along the length of the column can employ temperature measurement elements placed upstream and downstream of the column to provide feedback.

FIG. 1 shows an embodiment of a thermal system 10 including a multilayer microfluidic device 12, a plurality of thick-film heaters 14-1, 14-2, 14-3, and 14-4 (generally, 14), made of thick-film paste, integrated with the microfluidic device 12, and a separation column (i.e., fluidic channel or chromatography column) 18. Each thick film heater 14 is formed on an interior or exterior substrate layer of the microfluidic device 12. The heaters 14 may be on the same or on different layers. Each heater 14 is connected to electrical conduits 24 by an electrically conductive tap 26 on each end of that heater. Each of the four heaters is independently controllable (i.e., can be turned on and off independently of the other heaters).

In this embodiment, the heaters 14 surround the separation column 18 on four sides. The heaters 14-1 and 14-2 are connected in parallel to each other on opposite sides of the separation column, which extends longitudinally between the heaters 14-1, 14-2. The separation column 18 appears in phantom to illustrate that the column 18 may be fully enclosed within the layers of the microfluidic device 12. An ingress aperture 20 and an egress aperture 22 connect to the head end and exit end, respectively, of the column 18. The heaters 14-3 and 14-4 are connected in parallel to each other on ends of the separation column 18, extending generally perpendicular to the column 18 and the heaters 14-1 and 14-2. The heater 14-3 is at the head end of the separation column 18; the heater 14-4 is at the tail end.

The heater 14-1 is trapezoidal in shape, whereas the other heaters 14-2, 14-3, and 14-4 are rectangular. The wide end of the trapezoidal heater 14-1 is near the head end of the separation column 18 and the narrow end is at the tail end of the separation column 18. Other shapes for the heater 14-1 include triangular, geometries without straight edges, and any such shape that can produce a thermal gradient similar to that produced by the trapezoidal shape.

The manufacture of the microfluidic substrate with the one or more thick film heaters 14, 16 may use Low-Temperature Co-fired Ceramic (LTCC) or High-Temperature Co-fired ceramic (HTCC) tapes. Examples of LTCC tapes include the 951 Green Tape™ ceramic tape produced by DuPont Microcircuit Materials of Research Triangle Park, N.C., and LTCC ceramic tapes produced by ESL Electro Science of King of Prussia, Pa. LTCC technology enables low-temperature (about 850° C.) co-firing of the thick film heater and substrate layers of the multilayer microfluidic device. These microfluidic devices can be made, for example, of ceramic, silicon, silica, polymers, polyimide, stainless steel, or titanium. Examples of multi-layer microfluidic devices are described in U.S. patent application Ser. No. 13/321,696, titled "Chromatography Apparatus and Methods Using Multiple Microfluidic Substrates", the entirety of which is incorporated by reference herein. Examples of techniques for producing microfluidic devices with an integrated thermal gradient-producing thermal system are described in International Appln. No. PCT/US14/49616, filed Aug. 4, 2014, titled "Apparatus and Method for Creating a Static and Traversing Thermal Gradient on a Microfluidic Device", the entirety of which is incorporated by reference herein.

The trapezoidal heater 14-1, when operating, produces a thermal gradient 28 that becomes increasing warmer (i.e., lighter color) as the width of the heater decreases. The rectangular heaters 14-2, 14-3, and 14-4, when operating, produce a generally uniform thermal gradient 30. The combined effect of the four heaters 14 produces a spatial thermal gradient outside and along a length of the separation column 18. This spatial thermal gradient provides an exterior thermal environment of the separation column 18, and is configured to counteract a change in a property of this mobile phase as the mobile phases through the separation column 18, as described in more detail below. In this example, the combined effect is to produce an exterior thermal environment that is warmer at the egress end 22 of the column 18 than at the ingress end 20 to combat radial gradients in LC. In an alternative configuration, wherein the narrow end of the trapezoidal heater 14 is at the ingress end 20 of separation column 18, the spatial thermal gradient can be cooler at the egress end 22 than at the ingress end 20 to combat radial gradients in SFC or to maintain constant linear velocity in SFC. The combined effect can also operate to smooth out temperature spikes and droops.

Multiple independently operable heaters facilitate dynamic control of the thermal gradient within a fluidic channel. One heater 14-1 can serve as a primary heater, and another heater 14-2 as a supplemental heater; the role of the supplemental heater is to shape the spatial thermal gradient, for example, warmer temperatures near the inlet with an exponential temperature decay towards the outlet, warmer at the inlet with a linear decay toward the outlet. This enables the generation of linear and exponential temperature curves along the length of the channel 18.

Figure 2:
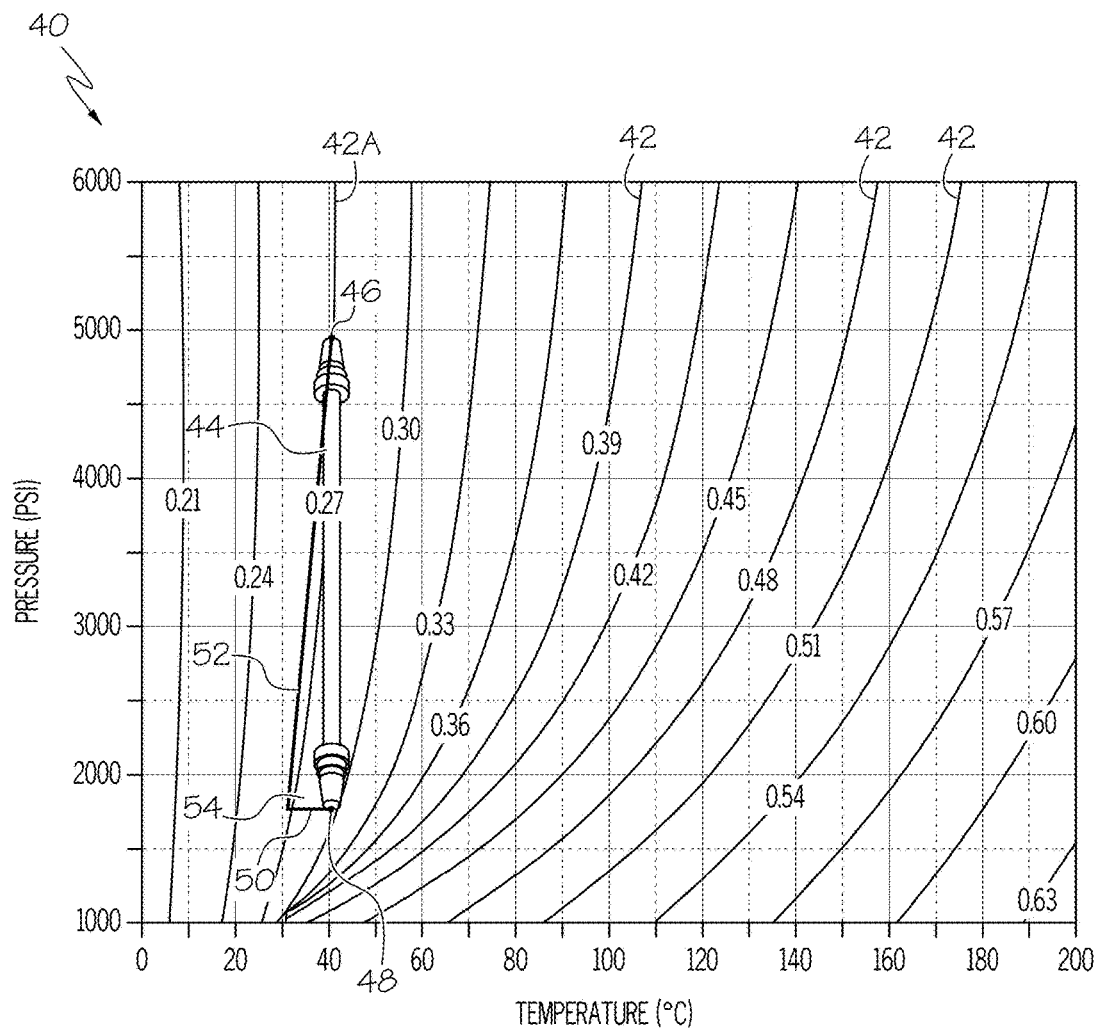
FIG. 2 is an example of a thermodynamic plot with a plurality of constant enthalpic curves used to estimate thermal heterogeneity of a mobile phase.

FIG. 2 shows an example of a thermodynamic plot 40 with a plurality of constant enthalpic (or isenthalpic) curves 42. Each isenthalpic curve 42 has an associated scalar quantity representing a measure of the thermodynamic potential of a particular mobile phase (e.g., CO2/MeOH). On the y-axis is pressure in pounds per square inch (psi); on the x-axis is temperature in degrees Centigrade.

The thermodynamic plot 40 can serve as a tool for quantifying the extent of thermal heterogeneity of a particular mobile phase flowing through a separation column. A separation column 44 is superimposed upon the plot 40 along a constant temperature (i.e., the temperature at the inlet 46 of the column 44 is the same as the temperature at the outlet 48 of the column 44). At this constant temperature, a drop in pressure occurs along the column from the inlet 46 to the outlet 48 of approximately 3000 psi. The placement of the column 44 on the plot 40 is such that the column inlet 46 falls on one of the isenthalpic curves (here, curve 42A). This isenthalpic curve 42A diverges from the column 44. A constant pressure line 50 is drawn from column outlet 48 to the isenthalpic curve 42A. This line 50 represents a measure of the radial thermal gradient formed within the mobile phase at the column outlet 48. A near-hypotenuse 52 drawn on the isenthalpic curve 42A completes a triangle 54, with the line 50 and column 44 as the other two sides of the triangle 54. The area of the triangle corresponds to the magnitude of an expected radial thermal gradient (for example, a large triangle area predicts a more significant thermal gradient than a small triangle area). A technique for using thermodynamic plots to estimate thermal heterogeneity in mobile phases is described in U.S. Prov. Appl. No. 61/992,016, filed on May 12, 2014, titled "Method for Estimating Temperature Variation in Chromatography using Thermodynamic Plots and Uses Thereof", the entirety of which is incorporated by reference herein.

Figure 3:
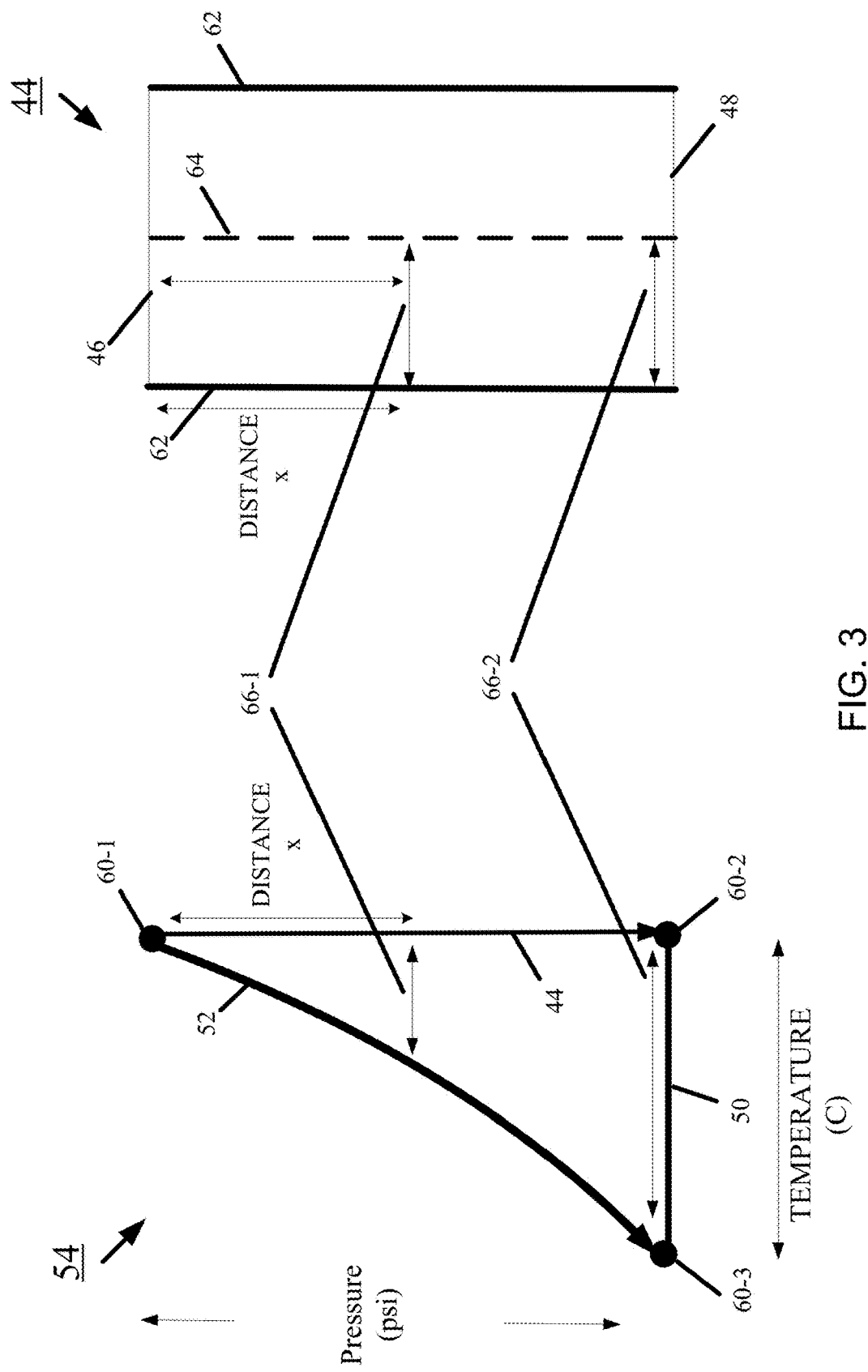
FIG. 3 is an example of a triangle drawn on a thermodynamic plot used for estimating thermal heterogeneity of a mobile phase along a length of a column.

FIG. 3 shows the triangle 54 of FIG. 2 adjacent the column 44 to illustrate a correspondence between the triangle 54 and the thermal heterogeneity of the mobile phase at different distances along the column 44. The column 44 forms one side of the triangle 54, the constant pressure line 50 forms a second side, and the near-hypotenuse 52, which runs along the isenthalpic curve 42A, forms the third side. Vertex 60-1 of the triangle 54 is at the inlet of the column 44, vertex 60-2 is at the outlet of the column 44, and vertex 60-3 is at the outlet of the column on the isenthalpic curve 42A. The coordinates of vertex 60-1 may be notated as Pinlet, Tinlet; the coordinates of vertex 60-2, as Poutlet, Toutlet; and the coordinates of vertex 60-3, as Poutlet, Tadiabatic. The temperature Tinlet is equal to the temperature Toutlet because, for the purpose of quantifying thermal heterogeneity, the column 44 is presumed to be in an oven at a constant temperature.

Adjacent the triangle 54 is a cross-sectional diagram of the column 44 with an isothermal wall 62. This isothermal wall 62 corresponds to the column 44 of the triangle 54. A dashed line 64 bisects the column 44 and runs along the column center. The column inlet 46 is shown at the top, and the column outlet 48 is shown at the bottom. The pressure at the inlet 46 is Pinlet, and at the outlet 48 is Poutlet.

The triangle 54 is used to quantify a first temperature difference 66-1 at a distance x from the column inlet 46. This temperature difference is measured from the column 44 to the near-hypotenuse 52. Within the column 44, this temperature difference 66-1 (i.e., radial thermal gradient) occurs between the column center 64 and the isothermal wall 62 at a distance x from the column inlet 46. The triangle 54 is also used to quantify a second temperature difference 66-2 at the column outlet 48. Within the column 44, this temperature difference 66-2 (i.e., radial thermal gradient) occurs between the column center 64 and the isothermal wall 62 at the column outlet 48. The radial thermal gradient (i.e., second temperature difference 66-2) at the column outlet 48 is greater than the radial thermal gradient (i.e., first temperature difference 66-1) at the column inlet 46; the two temperature differences 66-1, 66-2 thus provides two data points of an internal thermal gradient along the length of the column 44. In general, the temperature differences between the column 44 and the hypotenuse 52 of the triangle 54 along the full length of the column 44 may describe a profile of an internal thermal gradient formed in the mobile phase passing from the column inlet 46 to the column outlet 48.

For example, consider that the temperature difference 66-1 at distance x is 10° C. and the temperature difference 66-2 at the column outlet is 25° C., these data points demonstrate the extent of the temperature change experienced by the mobile phase from to the column inlet 46 to the column outlet 48. A thermal system, such as thermal system 10 of FIG. 1, can be used to produce a spatial thermal gradient external to the column 44 that substantially matches the internal thermal gradient formed within the column 44. This matching of internal and external thermal gradients operates to mitigate or avert formation of a radial thermal gradient within the mobile phase.

In this particular example, the use of an enthalpic curve is predictive of a cooling thermal gradient, which is appropriate for a compressible mobile phase. For an incompressible fluid (LC), an enthalpic curve would sweep to the right, signifying a thermal gradient that is warmer near the outlet.

Figure 4A:
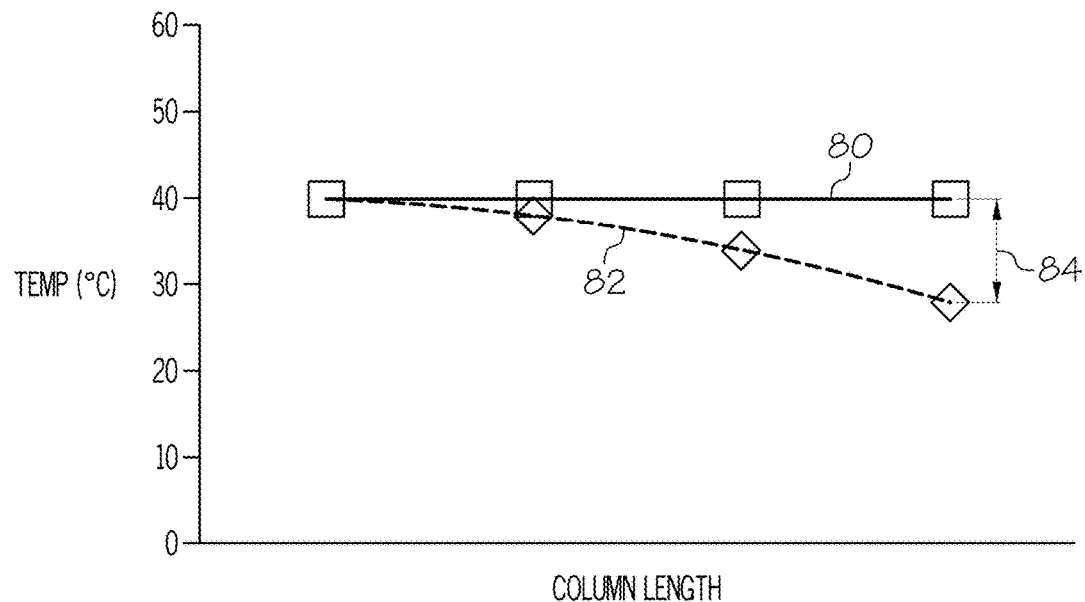
FIG. 4A is an example graph showing prior art operation wherein a column is kept within an oven at a constant temperature while a mobile phase passes through the column, leading to formation of a radial thermal gradient in the mobile phase.
Figure 4B:
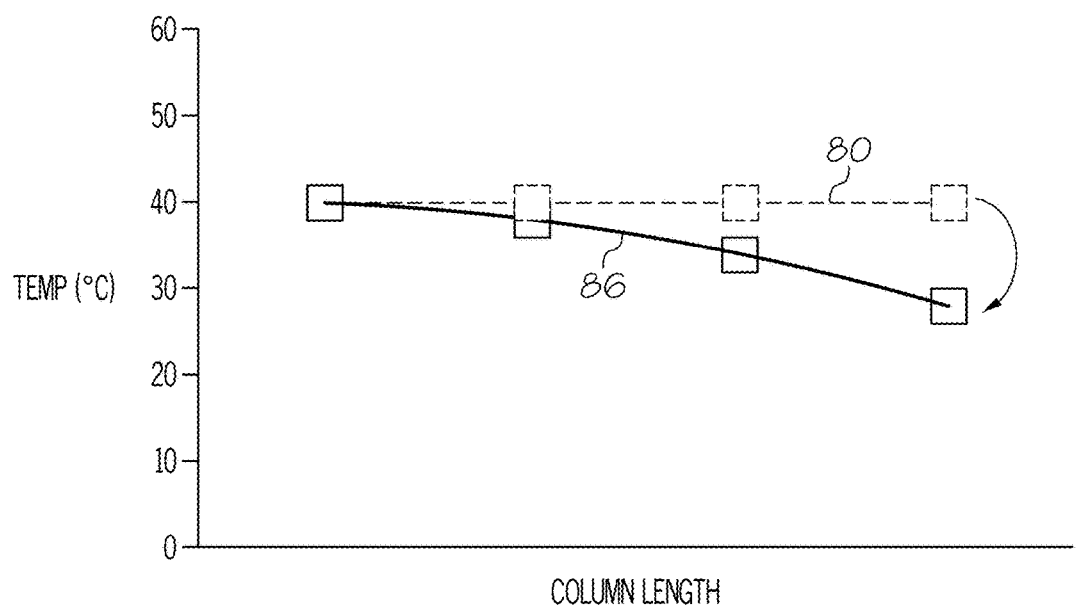
FIG. 4B is an example graph illustrating prevention of the formation of a radial thermal gradient by the use of an external spatial thermal gradient that substantially matches the thermal gradient of the mobile phase.

FIG. 4A and FIG. 4B are plots illustrating, by comparison, the principles of matching the internal and external thermal gradients in order to mitigate or avert formation of a radial thermal gradient within the mobile phase. FIG. 4A shows a prior art operation wherein the column is kept within an oven at a constant temperature. Graph 80 represents this constant temperature along the length of the column. Graph 82 represents the temperature of the mobile phase as the mobile phase passes through the column. In this example, the mobile phase becomes cooler the farther the mobile phase moves along the column, a condition that can arise when a compressible mobile phase decompresses. A radial thermal gradient 84 forms within the mobile phase.

FIG. 4B shows the prevention of the formation of a radial thermal gradient by the use of an external spatial thermal gradient that matches the thermal gradient of the mobile phase. Graph 80 (in phantom) corresponds to the technique of maintaining a constant oven temperature within which to keep the column. Graph 86 represents the use of an external spatial thermal gradient to match the temperature of the mobile phase as the mobile phase passes through the column. This spatial thermal gradient causes the external temperature of the column to match the internal temperature (as shown in the graph 82 of FIG. 4A); this matching is depicted by having the graph 86 superimposed upon and exactly covering the graph 82. As a result of the matching, no radial thermal gradient forms.

Figure 5:
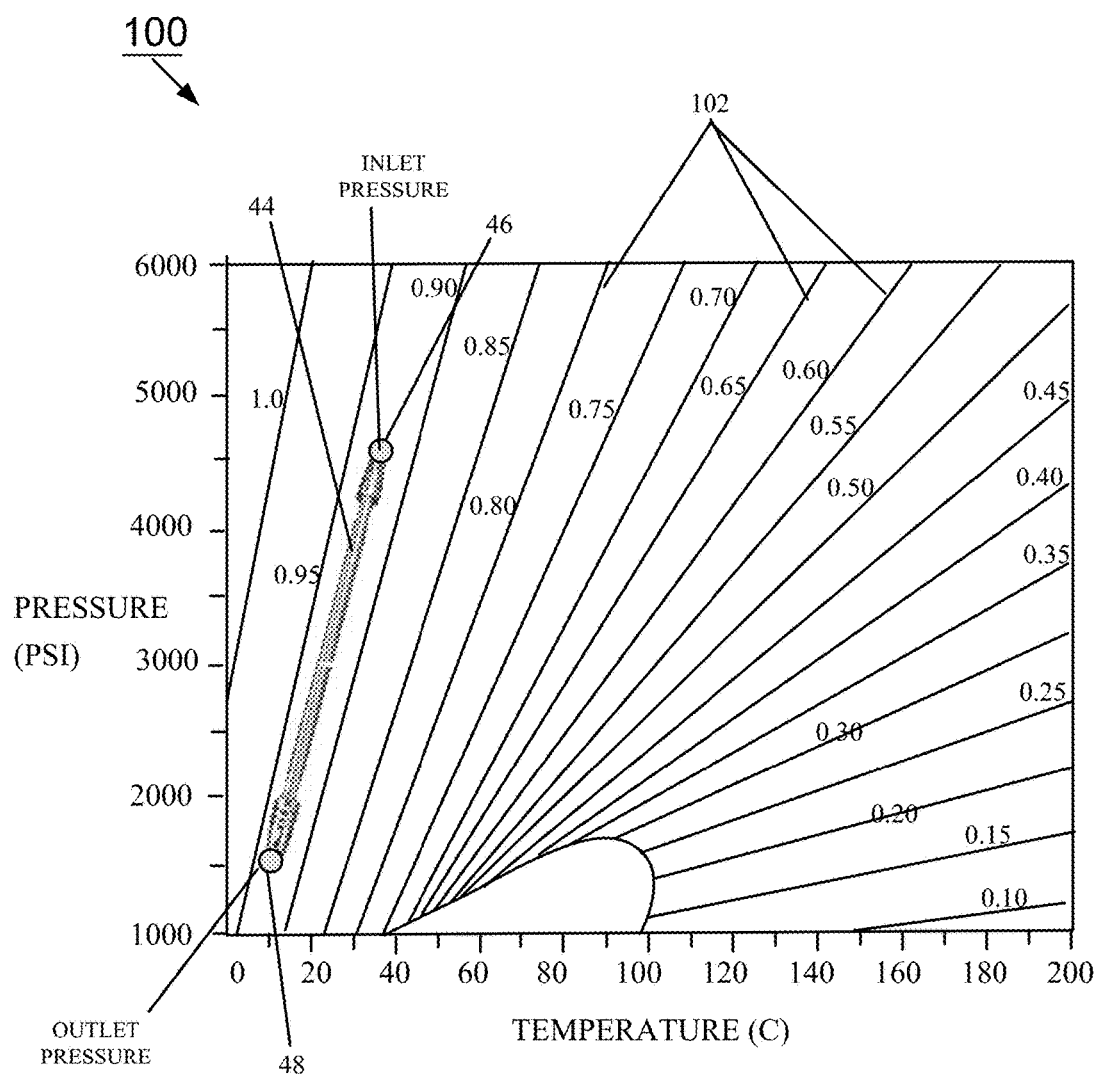
FIG. 5 is an example of a thermodynamic plot with a plurality of isopycnic curves and a chromatography column superimposed on the plot.

FIG. 5 shows an example of a thermodynamic plot 100 with a plurality of isopycnic ("of the same density") curves 102 with a chromatography column 44 superimposed on the plot. Each isopycnic curve has an associated scalar quantity representing a measure of the density of a particular mobile phase (e.g., $CO_2$/with 10% MeOH). On the y-axis is pressure in psi; on the x-axis is temperature in degrees Centigrade. A separation column 44 is superimposed upon the plot 100 along or parallel to an isopycnic curve 102.

The thermodynamic plot 100 can serve as a tool for quantifying a thermal gradient for maintaining the mobile phase at a constant density. Placement of the inlet 46 and outlet 48 of the column 44 on the same isopycnic curve 102 ensures that the density of the mobile phase remains substantially constant throughout the column 44. The system pressure and temperature at the inlet 46 the column 44 serve as a guide as to the isopycnic curve 102 with which to align the column 44. The outlet temperature can be acquired from the thermodynamic plot 100 (the system outlet pressure serving as a guide to how far to extend the column 44 along the isopycnic curve 102). The inlet and outlet temperatures taken from the plot 100 provide the thermal gradient. For example, in FIG. 5, the temperature of the column inlet 46 is approximately 35° C. and that of the column outlet 48 is approximately 10° C. The thermal gradient is a cooling one, dropping 25° C. across the length of the column 44.

A thermal system, such as thermal system 10 of FIG. 1, can be used to produce a spatial thermal gradient external to the column 44 that substantially matches the thermal gradient derived from an isopycnic plot. This matching of internal and external thermal gradients operates to maintain a substantially constant density of the mobile phase as the mobile phase moves through the length of the column 44. This substantially constant density results in a uniform linear velocity of the mobile phase throughout the column, which reduces or prevents chromatographic band broadening.

Figure 6A:
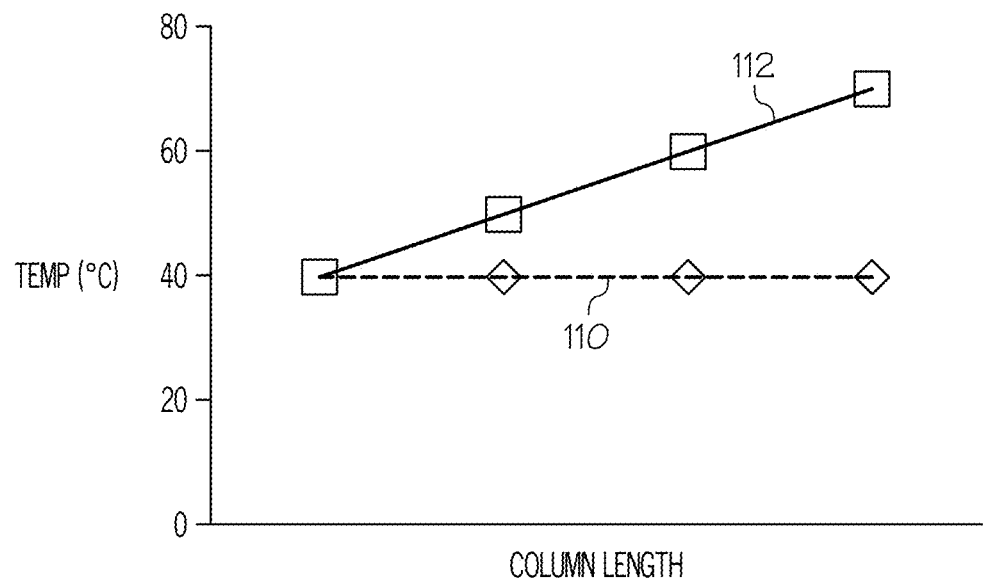
FIG. 6A is an example graph showing prior art operation wherein the column is kept within an oven at a constant temperature while a mobile phase passes through the column, leading to a decrease in density and corresponding increase in linear velocity of the mobile phase.
Figure 6B:
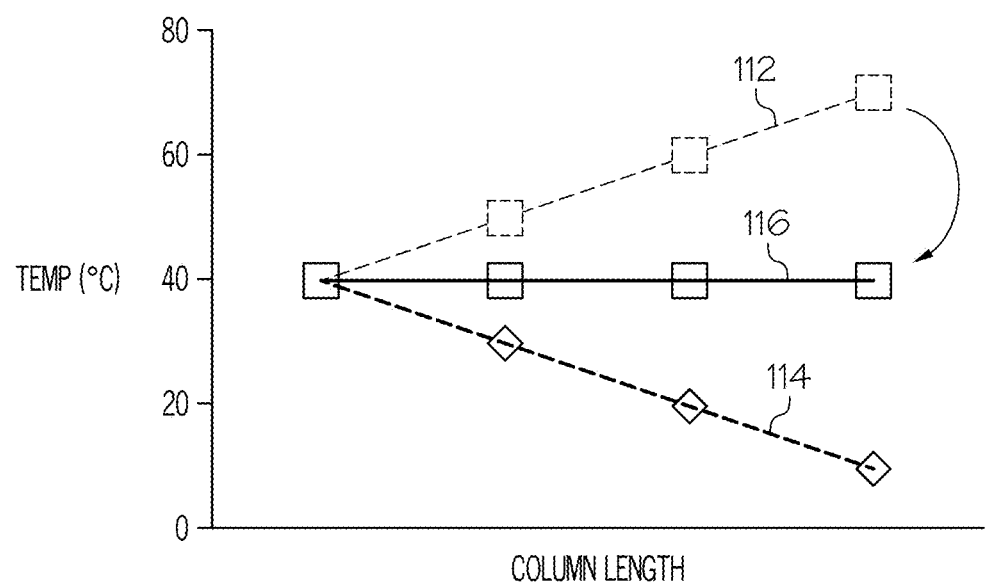
FIG. 6B is an example graph illustrating the results of using an external spatial thermal gradient to produce a uniform linear velocity, thereby reducing or preventing chromatographic band broadening.

FIG. 6A and FIG. 6B are plots illustrating, by comparison, the principles of matching the an external spatial thermal gradient to a thermal gradient derived from an isopycnic plot (e.g., FIG. 5) in order to maintain a uniform linear velocity of the mobile phase. FIG. 6A shows a prior art operation wherein the column is kept within an oven at a constant temperature. Graph 110 represents this constant temperature along the length of the column. Graph 112, which is derived from an isopycnic plot, represents the linear velocity of the mobile phase as the mobile phase moves along the length of the column. In this example, the linear velocity of the mobile phase is increasing the further the mobile phase moves along the column, which can be attributable to a decrease in mobile phase density. The changing linear velocity can cause chromatographic band broadening because the linear velocity moves away from the minima of the Van Deemter curve.

FIG. 6B shows the results of using an external spatial thermal gradient to produce a uniform linear velocity, thereby reducing or preventing chromatographic band broadening. Graph 112 (in phantom) corresponds to the conventional increasing linear velocity of the mobile phase along the length of the column when the external temperature of the column 44 is held constant (as shown in FIG. 6A). Graph 114 represents the use of an external spatial thermal gradient to maintain a constant density of the mobile phase along the length of the column. In this example, the outlet of the column is cooled relative to the column inlet, such that temperatures decrease along the length of the column in a manner that follows an isopycnic line (FIG. 5). This matching of the external cooling temperature gradient to the isopycnic line operates to maintain the density of the mobile phase at a constant value (i.e., keep the density from falling), thereby maintaining a constant velocity of the mobile phase. Graph 116 shows the uniform linear velocity of the mobile phase resulting from the cooling spatial thermal gradient. As a result of the uniform linear velocity, the extent of chromatographic band broadening is reduced or eliminated compared to when the linear velocity increases because the linear velocity does not move away from the Van Deemter minima.

Figure 7A:
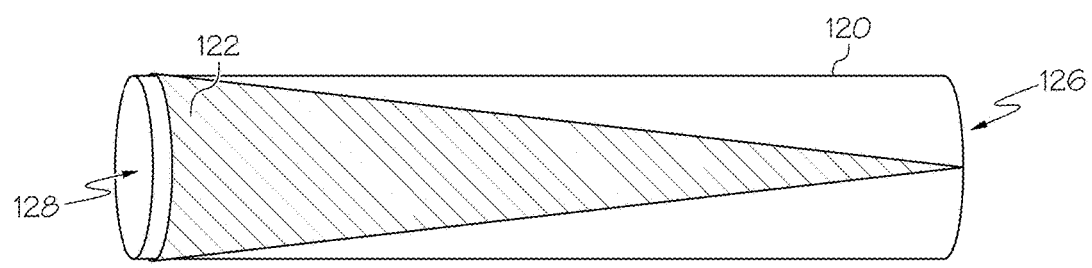
FIG. 7A is a diagram of an analytical scale chromatography column having a triangular-shaped resistive heating element on one side of the column.

The aforementioned principles of matching external and internal thermal gradients for fluidic channels extend to other types of separation columns. FIG. 7A shows one side of an embodiment of an analytical scale packed-bed chromatography column 120 (e.g., 1 mm-5 mm ID). A triangular-shaped resistive heating element 122 is disposed on an external surface of the chromatography column. The resistive heating element 122 is a metallic surface that tapers to a point at one end of the column (which can be the column inlet or outlet, depending on the type of spatial gradient desired). The region of the column 120 left uncovered by the heating element 122 is thermally non-conductive. Like the trapezoidal-shaped heater 14 of FIG. 1, the resistive heating element 122 is warmer at the narrow tip than at the wider end when operating. The isosceles triangle shape of the heating element 122 ensures better temperature distribution in the radial direction on the 3-D cylindrical column 120 than would the right triangle shape of the heater 14 of FIG. 1.

Figure 7B:
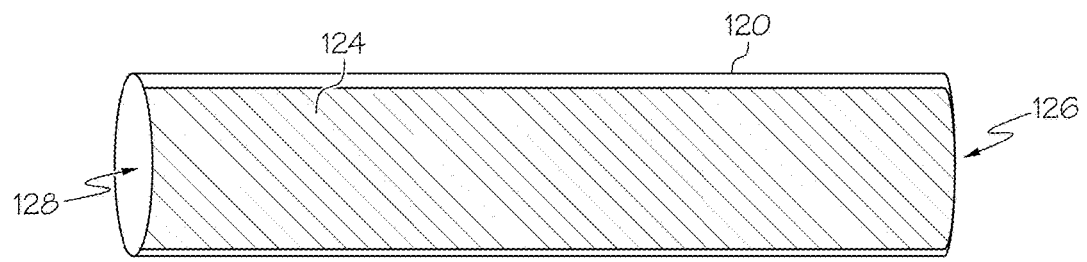
FIG. 7B is a diagram of the analytical scale chromatography column of FIG. 7A having a rectangular-shaped heating element on an opposite side of the column.

FIG. 7B shows an opposite side of the analytical scale chromatography column 120 of FIG. 7A. On this side is a rectangular-shaped resistive heating element 124. This heating element 124 is thermally insulated from the other heating element 122 of FIG. 7A. Like the rectangular-shaped heater 16 of FIG. 1, this resistive heating element 124 produces a generally uniform thermal gradient and can be used as a supplemental heater to set a base temperature.

The combined effect of the heaters 122, 124 of FIG. 7A and FIG. 7B, respectively, produces a spatial thermal gradient on the exterior of the separation column 18. In this example, the combined effect is to produce an exterior surface that is warmer at the one end 126 of the column 18 than at the opposite end 128. Example implementations of the heaters 122, 124 can include, but are not limited to, heating elements that are screen-printed, laminated, or integrated to the column surface, thick film pastes, mica heaters, and flexible heating circuits.

Figure 8:
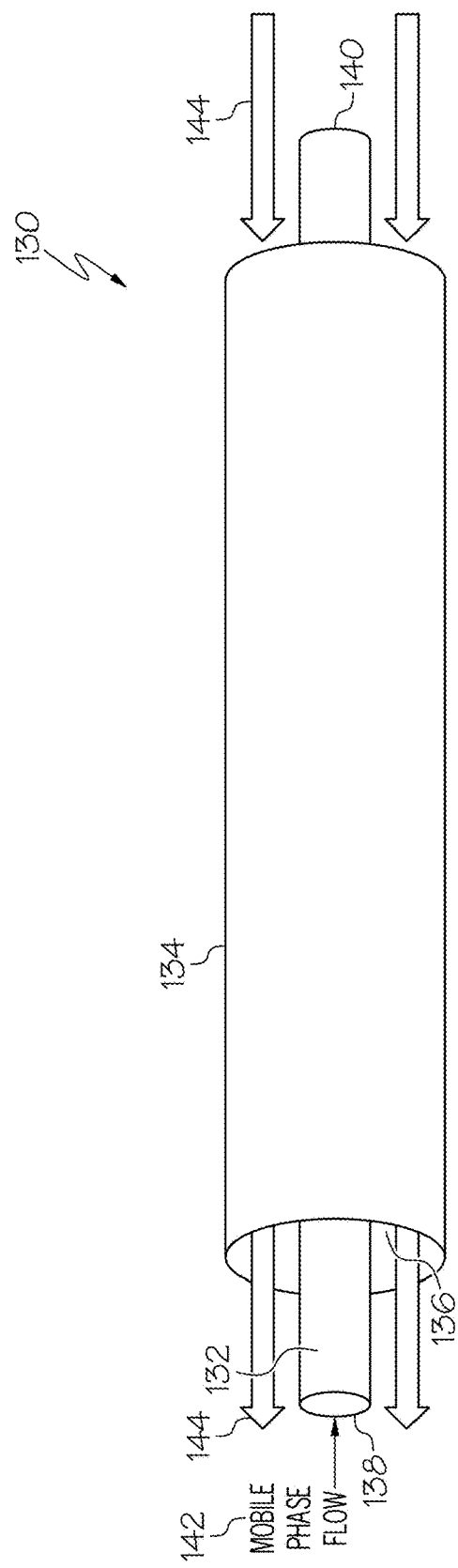
FIG. 8 is a diagram of an analytical scale chromatography column surrounded by a heated column sleeve, wherein mobile phase passes through the column in one direction and cooling gas flows around the column within the heated sleeve in an opposite direction.

FIG. 8 shows an embodiment of a thermal system 130 for producing an external spatial thermal gradient for an analytical (or preparative) scale chromatography column 132. A heated column sleeve 134 surrounds the chromatography column 132. The column sleeve 134 may be heated by thermal elements disposed remotely to and in thermal communication with thermally conductive material on the column sleeve 134. Alternatively, such thermal elements may be disposed in direct physical contact with a surface of the sleeve. Examples of heaters for heating the column sleeve 134 include, but are not limited to, a flex heating circuit, pastes disposed on a thermally conductive surface, mica heaters, and a remotely heated block of thermally conductive material (for example, a thermoelectric device can be disposed remotely with respect to the sleeve, having a thermal connection (e.g., a heat pipe) to the block of thermally conductive material).

An air gap 136 surrounds the chromatography column 132 and separates the sleeve 134 from the external surface of the chromatography column 132. A mobile phase 142 flows into an inlet end 138 of the chromatography column 132, towards an outlet end 140. A cooling gas 144 flows through the air gap 136 between the sleeve 134 and the column 132 in a direction opposite the direction of mobile phase flow, starting at the column outlet 140 and flowing towards the column inlet 138. Heat from the heated sleeve 134 warms the gas 144 as the gas flows toward the inlet end 138 of the column 132. The external spatial thermal gradient produced by the combination of the heated sleeve 134 and cooling gas 144 is warmer at the column inlet 138 than at the column outlet 140. The external spatial thermal gradient may be designed to maintain a substantially constant density of the mobile phase as the mobile phase cools while flowing through the length of the column 132. This embodiment facilitates simple and inexpensive removal of the column 132 from the heating apparatus because the heater may not be physically coupled to the column 132. Further, the embodiment of FIG. 8 can be implemented separately or together with the embodiment of FIGS. 7A-7B.

Although described in connection with heaters, cooling elements disposed on or remotely coupled to the sleeve 134 can operate to cool the sleeve 134. In addition, a warming, ambient temperature, or cooled gas can flow through the air gap.

Figure 9:
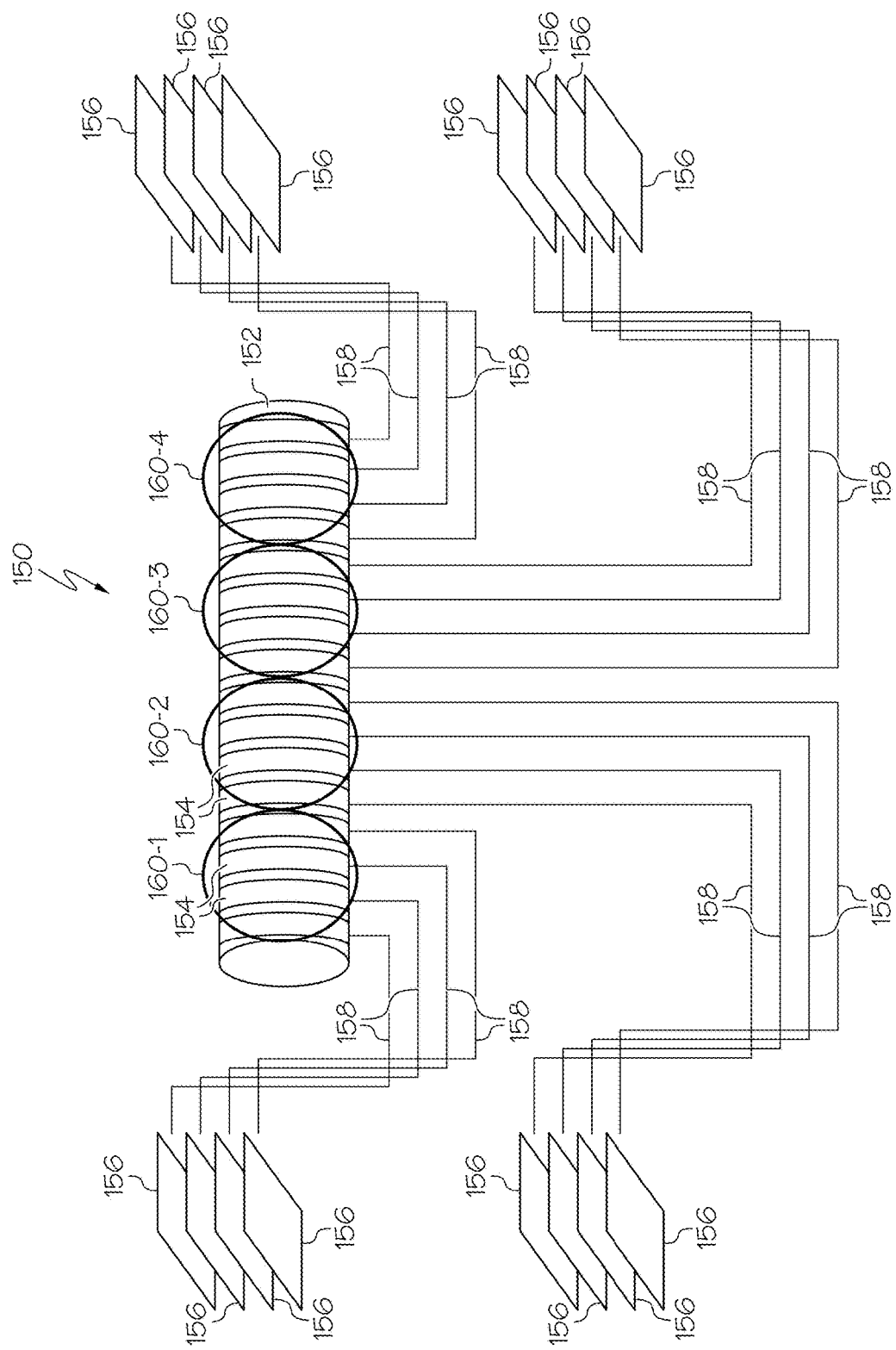
FIG. 9 is a diagram of an embodiment of an analytical scale chromatography column having a plurality of discrete, independently operable resistive heater elements wrapped circumferentially around a surface of the column.

FIG. 9 shows of an embodiment of a thermal system 150 for producing a spatial thermal gradient around the exterior of an analytical (or preparative) scale chromatography column 152. Wrapped circumferentially around the chromatography column 152 is a plurality of spatially separated discrete temperature heating elements 154. The heating elements 154 can be metallic rings or other structures that encircle the column 152. The elements can be made of metals of high thermal conductivity, for example, Ag and Cu, or non-metallic compounds, for example, diamond, or highly thermally conductive ceramic, for example, alumina. The heating elements 154 may be disposed on an exterior surface of the chromatography column 152, on the interior of a column heating compartment, or on a sleeve (such as the heated sleeve 134 of FIG. 8) surrounding the column 152. Each discrete heating element 154 may be individually operable. Each heating element 154 is controlled by a remote heater 156 thermally coupled to that heating element 154 by a heat-transfer device ("heat pipe") 158. Alternatively, the remote heaters 156 can be cooling devices, with each heating element 154 instead being a cooling element. The remote heaters (or coolers) 156 can be implemented with a stack of Peltier elements. Peltier elements enable generation of temperature gradients over a wide range of temperatures, from extreme cold to high heat.

In an alternative embodiment, the heating elements 154 can be themselves be heaters (e.g., screen-printed thick film pastes), each almost fully encircling the column 120. Further, the remote heaters 156 and corresponding heating elements 154 can be grouped to produce a spatial thermal gradient with multiple thermal zones, for example, zones 160-1, 160-2, 160-3, and 160-4 (generally, 160), each zone 160 consisting of four heating (or cooling) elements 154. Using fine discrete metallic devices enables high resolution temperature profiles at precise locations along the column length.

The number of heaters (or coolers) 156 and associated elements 154 determines the precision and resolution of the desired temperature gradient. Together, the heating (or cooling) elements 154 may be cooperatively controlled to produce a cooling or warming thermal gradient along the exterior surface (or wall) of the column 152 from the inlet to the outlet. In addition, the spatial thermal gradient can be statically maintained to attain a particular temperature profile. Alternatively, the spatial thermal gradient can be dynamically controlled to vary or move the spatial thermal gradient, as desired, by individually controlling the energy flowing to and from the elements 154 through the heat pipes 158. In a further embodiment the dynamically controlled spatial thermal gradient is automatically responsive to thermodynamic modeling software. Alternatively, the dynamic control of the spatial thermal gradient is based on a lookup table or database containing thermodynamic properties. The dynamic changes can be made throughout the duration of the separation by a temperature controller (not shown) in communication with the heaters (or coolers) 156. Such dynamic changes enable the thermal system 150 to continuously adapt during a pressure/temperature/composition gradient.

Figure 10:
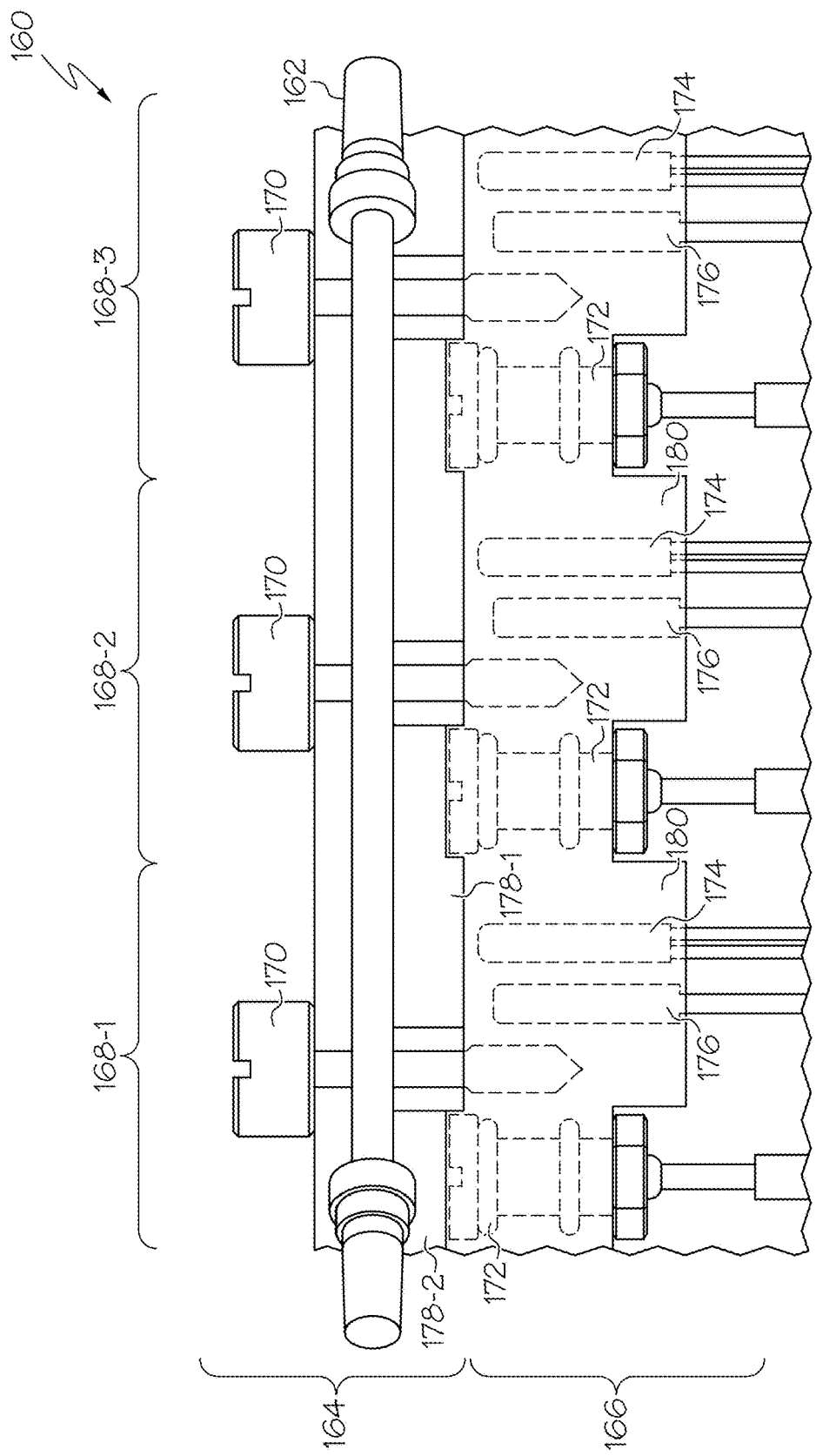
FIG. 10 is a transparent side view of an embodiment of a multi-zone thermal system, including a column block coupled to a thermal block, used to produce a spatial thermal gradient around a column.

FIG. 10 shows a transparent side view of an embodiment of a multi-zone thermal system 160 that can be used to produce an external spatial thermal gradient around an analytical (or preparative) scale chromatography column 162. The multi-zone thermal system 160 includes a thermally conductive column block 164 coupled to, and in thermal communication with, a thermally conductive thermal block 166. The chromatography column 162 passes through the column block 164. (Although described with respect to an analytical scale chromatography column, the multi-zone thermal system can be used to produce a spatial thermal gradient for a fluidic channel embedded in the column block 164). A thermal gasket (not shown) may be disposed at select regions between the thermal block 166 and the column block 164.

This embodiment of the multi-zone thermal system 160 has three thermal zones 168-1, 168-2, and 168-3 (generally, thermal zone 168), although other embodiments can have as few as two or more than three thermal zones. Each thermal zone 168 may include a retention mechanism 170 to hold the portion of the column block 164 in that zone in thermal communication with the portion of the thermal block 166 also of that zone. The retention mechanism 170 may include a screw that enters an appropriately sized opening in a top side of the column block 164, passes entirely through the column block 164, and fastens into an appropriately sized opening in a top side of the thermal block 166.

The thermal block portion of each thermal zone 168 includes a thermistor assembly 172, a heater 174, and a safety switch 176. In each thermal zone 168, the heater 174 and safety switch 176 within the thermal block 166 are disposed near and directly opposite a first region 178-1 of the column block 164, and the thermistor assembly 172 is disposed directly opposite a second region 178-2 of the column block 164. The thermistor assembly 172 is in thermal communication with the second region 178-2 of the column block 164 and may be substantially thermally isolated from the thermal block 166. This thermal isolation ensures that the temperature of the column block 164 of each thermal zone, as measured by the thermistor assembly 172, is substantially uninfluenced by the temperature of the thermal block portion of that thermal zone. In addition, each thermal zone 168 is insulated from its neighboring thermal zone or zones by a thermal insulation block 180.

In brief overview, circuitry actively controls the temperature of the thermal block 166 in each zone 168 by controlling operation of the heater 174 in that zone. Each zone 168 may have a different temperature setting, thereby producing a spatial thermal gradient along the length of the column block 164. The safety switch 176 in each zone 168 measures the temperature of the thermal block 166 near the heater 174 of that zone 168, and may operate to disable the heater 174 should its measured temperature exceed a threshold. The thermally conductive thermal block 166 conducts the heat generated by the heater 174 to the column block 164, predominantly through the first region 178-1. The thermistor assembly 172 measures the temperature of the second region 178-2 of the thermal zone 168. This measured temperature closely or exactly corresponds to the temperature of the column 162 in that thermal zone 168, and may be used as feedback in a closed-loop system.

In this example, the chromatography column 162 passes through three thermal zones 168-1, 168-2, and 168-3 (generally, 168) of a thermal system. Each thermal zone 168 can have a different temperature setting, with the temperature settings decreasing from left to right along the length of the column 162. For example, the temperature setting in the leftmost thermal zone 168-1 can be 40° C., 30° C. in thermal zone 168-2, and 20° C. in the rightmost thermal zone 168-3. These particular temperatures settings produce an external spatial thermal gradient with a downward sloping profile. The spatial thermal gradient produced by the temperature settings causes a gradual decline in the column temperature from left to right along the length of the column 162.

Figure 11:
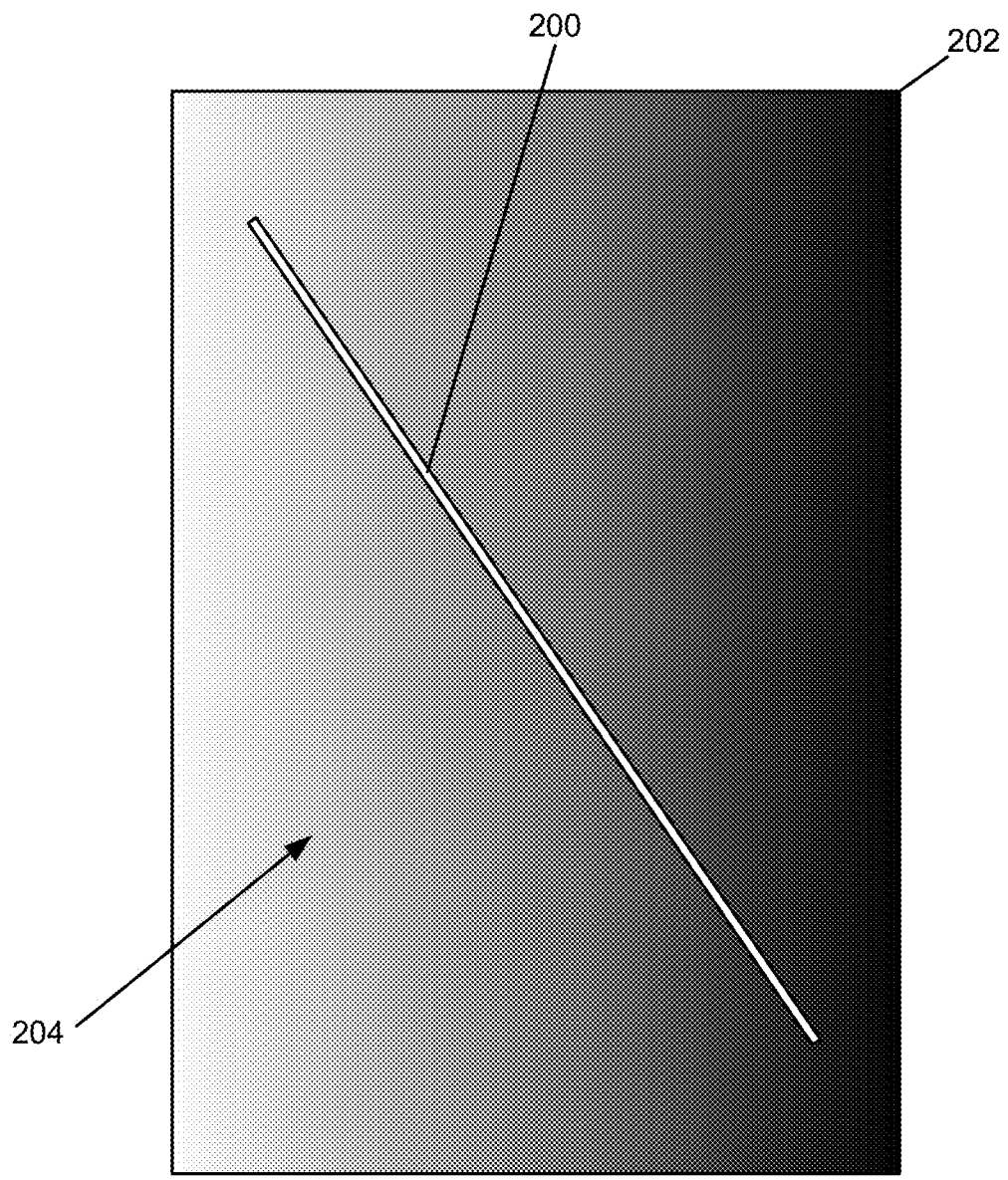
FIG. 11 is a diagram of an analytical scale column in thermal communication with a surface upon which a thermal gradient has already been formed.

FIG. 11 shows another embodiment in which a static thermal gradient is established along a length of a column 200 by placing the column 200 in thermal communication with a surface 202 on which a thermal gradient 204 is already established. In FIG. 11, warmer regions are lighter in color than darker regions, with the temperature gradient passing from warmer to cooler temperatures moving from left to right across the surface 202. Changing the angle of the column 200 relative to the thermal gradient 204 establishes different temperature gradient slopes along the length of the column 200. For example, positioning the column 200 parallel (horizontal in FIG. 11) to the thermal gradient direction establishes a steep slope, whereas positioning the column normal (vertical in FIG. 11) to the thermal gradient direction produces an isothermal condition along the length of the column 200.

It is to be understood that such terms like above, below, upper, lower, left, leftmost, right, rightmost, top, bottom, front, and rear are relative terms used for purposes of simplifying the description of features as shown in the figures, and are not used to impose any limitation on the structure or use of any thermal systems described herein. While the invention has been shown and described with reference to specific embodiments, it should be understood by those skilled in the art that various changes in form and detail may be made therein without departing from the spirit and scope of the invention as defined by the following claims.

What is claimed is:

1. A separation column assembly comprising:
    a tube with a bore packed with a stationary phase through which a mobile phase flows; and
    one or more thermal elements disposed remotely from and unattached to the tube, the one or more thermal elements being in thermal communication with an external surface of the tube for producing a spatial thermal gradient outside of and along a length of the tube;
    a sleeve disposed around the tube, the sleeve being open at both ends and separated from the tube by an air gap through which a gas flows, and wherein the one or more thermal elements are in thermally conductive communication with an outside surface of the sleeve; and
    a plurality of discrete, spatially separated strips of thermally conductive material disposed on and wrapped around the outside surface of the sleeve, and wherein the one or more thermal elements comprise a plurality of thermoelectric devices, each thermoelectric device being in thermal communication with one of the thermally conductive elements disposed on the sleeve by a heat-transfer device.

2. The separation column assembly of claim 1, wherein the one or more thermal elements comprise heating elements that heat the sleeve; and wherein the gas flowing through the air gap is a cooling gas.

3. The separation column assembly of claim 1, wherein the one or more thermal elements comprise cooling elements that cool the sleeve, and wherein the gas flowing through the air gap is at least as high as ambient temperature.

4. The separation column assembly of claim 1, wherein the bore of the tube has an inner diameter ranging between 1.0 and 5.0 mm, inclusively.

5. The separation column assembly of claim 1, wherein one or more of the thermal elements is configured to operate as a cooling device.

6. The separation column assembly of claim 1, wherein one or more of the thermal elements is configured to operate as a heating element.

7. The separation column assembly of claim 1 further comprising a thermal controller in communication with the one or more thermal elements.

8. The separation column assembly of claim 7, wherein the thermal controller is configured to dynamically control the spatial thermal gradient.

9. The separation column assembly of claim 7 further comprising a database in communication with the thermal controller, the database containing thermodynamic properties of the separation column assembly.

10. A separation column assembly comprising:
a tube with a bore packed with a stationary phase through which a mobile phase flows;
a plurality of discrete, spatially separated strips of thermally conductive material disposed on and wrapped around an external surface of the tube; and
one or more thermal elements disposed remotely from the tube, each of the one or more thermal elements being in thermal communication with one of the strips of thermally conductive material by a heat-transfer device, the one or more thermal elements producing a spatial thermal gradient outside of and along a length of the tube by controlling temperature of each strip of thermally conductive material disposed on and wrapped around the external surface of the tube.

11. The separation column assembly of claim 10, further comprising a sleeve disposed around the tube, the sleeve being open at both ends and separated from the tube by an air gap through which a gas flows, and wherein the one or more thermal elements are in thermally conductive communication with an outside surface of the sleeve.

12. The separation column assembly of claim 10, wherein the one or more thermal elements comprise heating elements that heat one or more of the strips of thermally conductive material.

13. The separation column assembly of claim 10, wherein the one or more thermal elements comprise cooling elements that cool one or more of the strips of thermally conductive material.

14. The separation column assembly of claim 10, wherein the one or more thermal elements comprise a plurality of thermoelectric devices.

15. A separation column assembly comprising:
a tube with a bore packed with a stationary phase through which a mobile phase flows;
one or more thermal elements disposed remotely from and unattached to the tube, the one or more thermal elements being in thermal communication with an external surface of the tube for producing a spatial thermal gradient outside of and along a length of the tube; and
wherein the one or more thermal elements are selected from the group consisting of:
spatially separated discrete temperature heating elements wrapped circumferentially around a chromatography column of the separation column assembly; and
spatially separated discrete temperature cooling elements wrapped circumferentially around a chromatography column of the separation column assembly.

16. The separation column assembly of claim 15, wherein the one or more thermal elements are disposed on at least one of: an external surface of the chromatgraphy column; and an interior of a column heating compartment.

17. The separation column assembly of claim 15, wherein each heating element has a corresponding remote heater and is individually operable and controlled by the corresponding remote heater, the remote heater for each heating element being thermally coupled to that heating element by a heat transfer device.

18. The separation column assembly of claim 15, wherein each cooling element has a corresponding remote cooling device and is individually operable and controlled by the corresponding remote cooling device.

* * * * *